(12) United States Patent
Slutter et al.

(10) Patent No.: US 11,460,381 B2
(45) Date of Patent: Oct. 4, 2022

(54) SAMPLE GRINDER

(71) Applicant: SPEX SamplePrep, LLC, Metuchen, NJ (US)

(72) Inventors: Warren Stephen Slutter, Metuchen, NJ (US); Greg King, Metuchen, NJ (US); Eric Smith, Metuchen, NJ (US); Lea Anderson-Smith, Metuchen, NJ (US); Jim Distabile, Metuchen, NJ (US); Geoff Cohen, Metuchen, NJ (US); Andrew Beck, Metuchen, NJ (US)

(73) Assignee: SPEX SAMPLEPREP, LLC, Metuchen, NJ (US)

( * ) Notice: Subject to any disclaimer, the term of this patent is extended or adjusted under 35 U.S.C. 154(b) by 324 days.

(21) Appl. No.: 16/682,969

(22) Filed: Nov. 13, 2019

(65) Prior Publication Data

US 2020/0150005 A1    May 14, 2020

Related U.S. Application Data

(60) Provisional application No. 62/760,457, filed on Nov. 13, 2018.

(51) Int. Cl.
| | | |
|---|---|---|
| *G01N 1/00* | (2006.01) | |
| *G01N 1/28* | (2006.01) | |
| *C12M 1/33* | (2006.01) | |
| *B01L 3/00* | (2006.01) | |
| *C12N 15/10* | (2006.01) | |

(52) U.S. Cl.
CPC ............ *G01N 1/286* (2013.01); *C12M 45/02* (2013.01); *B01L 3/508* (2013.01); *C12N 15/1003* (2013.01); *G01N 2001/2866* (2013.01)

(58) Field of Classification Search
None
See application file for complete search history.

(56) References Cited

U.S. PATENT DOCUMENTS 5,464,773 A    11/1995  Melendez et al.
5,567,050 A *  10/1996  Zlobinsky ........... B01F 11/0008
                                                  366/110

OTHER PUBLICATIONS

International Search Report and Written Opinion, issued by International Searching Authority in corresponding International Application No. PCT/US2019/061280, dated Jun. 26, 2020.

(Continued)

*Primary Examiner* — Jyoti Nagpaul
(74) *Attorney, Agent, or Firm* — ArentFox Schiff LLP

(57) ABSTRACT

A bead beater homogenizer includes a shaft having a main body extending along a main axis and a distal connection body extending along a connection axis that is acutely angled with respect to the main axis, a motor configured to rotate the shaft about the main axis, a head rotatably connected to the distal connection body of the shaft, and a clamp secured to the head and configured to secure a sample vial holder configured to hold one or more sample vials therein, wherein rotational motion of the shaft about the main axis is translated into motion of the head in directions normal to the main axis. A sample vial holder having an internal network of channels defined within the housing through which a coolant can be passed to control a temperature of a vial disposed therein is also provided.

15 Claims, 13 Drawing Sheets

(56) References Cited

OTHER PUBLICATIONS

R. S. W. van de Wal et al., "Progress in 14C Dating of Ice at Utrecht", 2107b Nuclear Instruments & Methods in Physics Research B, Elsevier BV, Amsterdam, NL, vol. B52, Nos. 3/4, pp. 469-472, (1990).

* cited by examiner

SAMPLE GRINDER

CROSS-REFERENCE TO RELATED APPLICATIONS

The present application claims the benefit of the filing date of U.S. Provisional Patent Application No. 62/760,457, filed Nov. 13, 2018, the disclosure of which is hereby incorporated herein by reference.

BACKGROUND OF THE INVENTION

The present application relates to a mechanical disruption process of relatively small sample volumes and an improved, more robust system for more efficient disruption.

In the sample preparation market, a common way of disrupting, lysing, or grinding (pulverizing) a sample for further testing is by mechanical disruption. The typical goal of these processes includes one or more of the following: particle size reduction; facilitation of the extraction of DNA and RNA (Lyse), proteins, pesticides and other contaminates (i.e. metals or RoHS materials) by rupturing cells; and homogenization or mixing of a sample.

"Bead Beating" systems "grind" and pulverize a sample and use steel balls or other media like ceramics or glass to disrupt samples. The sample is shaken in some form with this process. The traditional "bead beater" instrument disrupts/lyses the sample by crushing or "beating" the sample between the top and bottom of a vial or between the balls or other media added to the vial during the process. Depending upon the instrument design, some of the sample lysing can occur between the media, from the media forces against the top and bottom of the sample container and from the media forces against the side walls of the sample container. The speed of such bead beater systems is typically in the 500-4,000 revolutions per minute range. This corresponds to 1,000 to 8,000 oscillations per minute. Large titer plate disruption devices have speeds ranging from 500-1,750 revolutions per minute. The motion found in bead beater products is a vertical or horizontal motion that forces the ball media to travel to and fro within the confines of the vertical height or width of the vial or a combination motion that imparts some vortexing of the sample and media to and fro within the sample vial.

The choice of using the bead beater depends on the sample vial size, sample size and sample characteristics. Tough samples like seeds, rice, corn kernels, organs and fibrous plants typically require larger, and heavier balls/media, while samples like bacteria, yeast and fungi, using smaller balls/media. Samples like leaves, soil and plant materials often require some investigation on the best device and media size.

Some instruments incorporate means for keeping samples cool during operation. This includes placing vials or titer plates in contact with cryo-blocks that are cooled prior to use. Some drawbacks associated with cryo-blocks are that they cannot maintain a particular temperature during use because they act as heat sinks, and their initial temperatures are often difficult to regulate, sometimes being too cold for certain samples. Improvements are needed.

While bead beaters have become important devices for sample grinding, further improvements are desired.

BRIEF SUMMARY OF THE INVENTION

A first aspect of the present invention is a bead beater homogenizer including a shaft having a main body extending along a main axis and a distal connection body extending along a connection axis that is acutely angled with respect to the main axis, a motor configured to rotate the shaft about the main axis, a head rotatably connected to the distal connection body of the shaft, and a clamp secured to the head and configured to secure a sample vial holder configured to hold one or more sample vials therein, wherein rotational motion of the shaft about the main axis is translated into motion of the head in directions normal to the main axis.

In other embodiments according to the first aspect, the main body of the shaft may intersect with the distal connection body at a bend or elbow in the shaft. The distal connection body may be disposed within a lumen defined by the head. Rotational motion of the shaft about the main axis may also be translated into oscillating motion of the head such that an end of the head closest to the main body of the shaft is pivoted toward and away from the main body of the shaft. The clamp may include a clamp base in which the sample vial holder can be disposed, a clamp arm connected to the clamp base, and a clamp latch connected to the clamp base, wherein engagement of the clamp latch with the clamp arm secures the sample vial holder to the head. The clamp arm may be pivotally connected to one side of the clamp base, and the clamp latch is pivotally connected to another side of the clamp base.

The clamp may be configured to accept a plurality of differently configured sample vial holders. The bead beater homogenizer may further include a plurality of differently configured sample vial holders. The differently configured sample vial holders may include at least two of: a first sample vial holder having only one well to hold one vial, a second sample vial holder having only two wells to hold two vials, a third sample vial holder having only three wells to hold three vials, a fourth sample vial holder having only four wells to hold four vials, a fifth sample vial holder having only five wells to hold five vials, a sixth sample vial holder having only six wells to hold six vials, and a seventh sample vial holder having at least one well to hold a vial and an internal network of channels through which a coolant can be passed to control a temperature of a vial disposed therein.

The bead beater homogenizer may further include a sample vial holder defining an internal network of channels through which a coolant can be passed to control a temperature of a vial disposed therein. The sample vial holder may include a housing defining a cavity configured to at least partially enclose a vial, and the internal network of channels may include an inlet channel, an internal channel adjacent the cavity, and an outlet channel connected for flow of the coolant. The sample vial holder may include a housing defining a cavity configured to at least partially enclose a vial, and a holder plug disposed in the cavity to seal the cavity from an external environment, the holder plug defining a cavity in which a vial can be seated. An empty pocket may be defined between an internal surface of the cavity of the housing and an external surface of the holder plug. The internal network of channels may include an inlet channel leading to the empty pocket, and an outlet channel leading away from the empty pocket, such that the inlet channel, the empty pocket, and the outlet channel define a passage through which a coolant can be passed to control a temperature of a vial disposed in the holder plug.

The bead beater homogenizer may further include a first bearing assembly disposed about the shaft between the head and the motor. The head ma further include a second bearing assembly disposed about the distal connection body of the shaft. The motor may include a third bearing assembly.

The bead beater homogenizer may further include a speed measurement disc rotationally coupled with the main body of the shaft, wherein the speed measurement disc defines a plurality of apertures in a circumferential periphery thereof, and an optical interrupter having two plates between which an IR signal is passed, wherein the circumferential periphery of the speed measurement disc is disposed between the plates of the optical interrupter such that the apertures cross a path of the IR signal. The bead beater homogenizer may further include a processor that receives signals corresponding to the interruption of the IR signal and that is configured to use the signals to calculate rotational speed of the shaft.

The sample vial holder may have end walls that cover at least 50% of the area of each end face of a vial, respectively. Rotational motion of the shaft about the main axis may rotate the distal connection body such that the distal connection body sweeps out an imaginary conical surface. Rotational motion of the shaft about the main axis may rotate the head in a circular path on an imaginary conical surface.

A second aspect of the present invention is a sample vial holder for use with a bead beater homogenizer, including a housing defining a cavity configured to at least partially enclose a vial, and an internal network of channels defined within the housing through which a coolant can be passed to control a temperature of a vial disposed therein.

In other embodiments according to the second aspect, the internal network of channels may include an inlet channel, an internal channel adjacent the cavity, and an outlet channel connected for flow of the coolant. The sample vial holder may further include a holder plug disposed in the cavity to seal the cavity from an external environment, the holder plug defining a cavity in which a vial can be seated. An empty pocket may be defined between an internal surface of the cavity of the housing and an external surface of the holder plug. The internal network of channels may include an inlet channel leading to the empty pocket, and an outlet channel leading away from the empty pocket, such that the inlet channel, the empty pocket, and the outlet channel define a passage through which a coolant can be passed to control a temperature of a vial disposed in the holder plug. The sample vial holder may further include a cover guard configured to cover an open end of the cavity.

A third aspect of the present invention is a bead beater homogenizer including a shaft having a main body extending along a main axis and a distal connection body extending along a connection axis that is acutely angled with respect to the main axis, a motor configured to rotate the shaft about the shaft axis and including a first bearing assembly, a head rotatably connected to the distal connection body of the shaft, wherein the head comprises a second bearing assembly disposed about the distal connection body of the shaft, a sample vial holder secured to the head, and a third bearing assembly disposed about the shaft between the head and the motor.

Other aspects of the present invention relate to the methods of using the above noted aspects, including operating the motor to rotate the shaft about its main axis.

DETAILED DESCRIPTION

Figure 1:
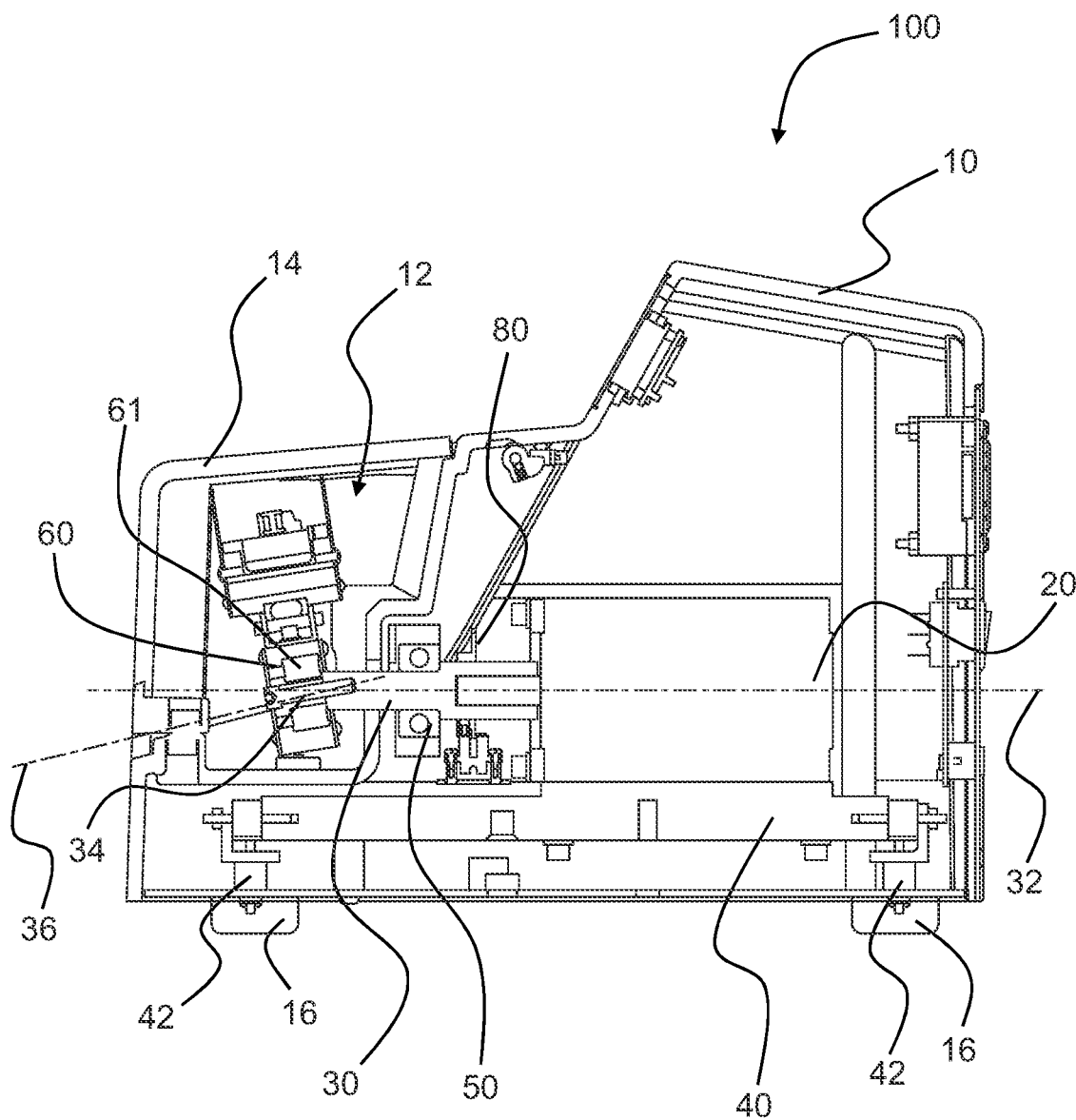
FIG. 1 is a cross sectional side view of a bead beater homogenizer in accordance with the present invention.
Figure 2:
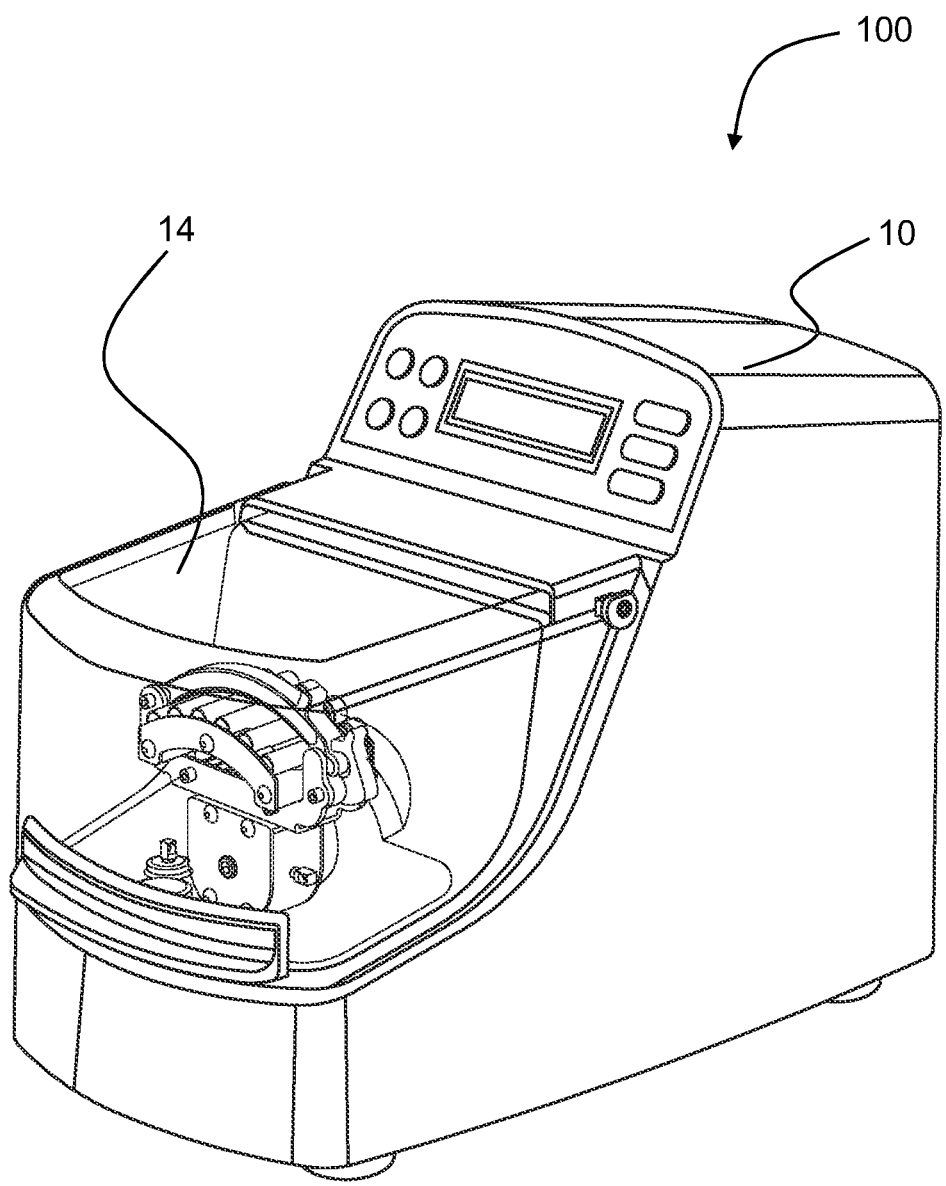
FIG. 2 is a perspective view of the bead beater shown in FIG. 1.

As shown in FIG. 1-7, an improved bead beater homogenizer 100 includes a housing 10 in which a motor 20 is disposed. Motor 20 is connected to an output shaft 30 that extends through the housing 10 into a sample chamber 12 shielded by a movable sample guard 14 that can be locked in place during use. Motor 20 is anchored to a damper plate 40 that is connected through dampening means 42 such as springs and shock absorbers to the bottom and sides of housing 10. There are shock absorbers on each end of the instrument to reduce the vibration effect. Housing 10 includes several pads 16 on its bottom to further dampen the vibrations emanating from use of bead beater 100 on an external surface. Bead beater 100 also allows the use of the instrument as a mixer with a mixing speed of 750 rpm and 1,000 rpm and homogenizing or grinding speeds of 2,000 rpm, 3,000 rpm and 4,000 rpm. Other speeds for either use are also contemplated.

Figure 3:
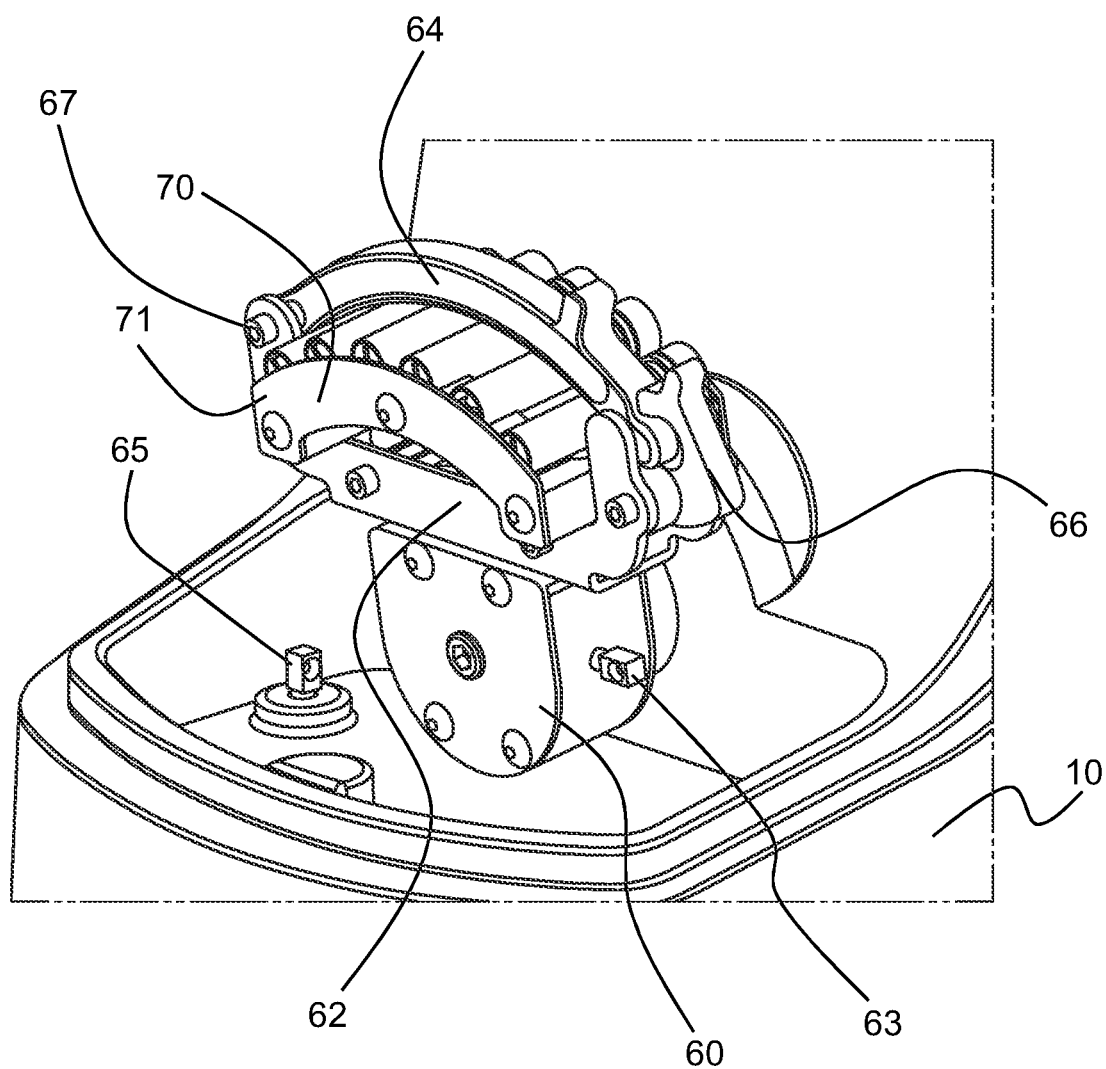
FIGS. 3-5 are perspective views of different sample vial sizes with different sample holders for each vial type as used in connection with the bead beater shown in FIG. 1.

Shaft 30 is rotated about its central longitudinal axis 32 through a bearing 50. A pin or screw 34 is fixedly connected to a distal end of shaft 30. An axis 36 of pin 34 is acutely angled to axis 32 of shaft 30, such that the overall shaft/pin construction includes a bend or elbow and so that rotation of shaft 30 causes pin 34 to move about or sweep out an imaginary conical surface. Pin 34 is disposed within a lumen of a sample connector or head 60 such that pin 34 can rotate within the lumen during use. Sample connector 60 is block-shaped with a flat surface facing motor 20. That flat surface is not orthogonal or normal to axis 32. Sample connector 60 is connected to housing 10 via a spring on each side of shaft 30, for example through anchors 63 on each side of sample connector 60 to anchors 65, as shown in FIG. 3. In this way, when shaft 30 is rotated about its central axis 32, pin 34 rotates eccentrically as indicated above and causes the lumen in sample connector 60 to move about the same imaginary conical surface, though without completely rotating about the axis of pin 34. During this movement, there is some lateral oscillation that occurs, which his dampened by springs. That is, sample connector 60 has an upward surface that remains facing generally upward throughout this motion. The springs anchor sample connector 60 to housing 10 to further guide its oscillating motion. The length of shaft 30, the angle and position of sample connector 60, and the strength of the springs are configured to create a more violent agitation process in order to more efficiently grind samples.

The rotational motion of shaft 30 about axis 32 causes sample connector 60 to move around a circle of the imaginary cone, such that it moves in all directions normal to axis 32. This also causes head to rock, pivot, or oscillate toward and away from the main body of shaft 30, i.e. where motor 20 is located. For example, while FIG. 1 depicts sample connector 60 tilted so that it is angled from the bottom left to the top right of the image, once pin 34 is rotated to its uppermost position, sample connector 60 will be angled from the top left to the bottom right of the image. Since sample connector 60 does not rotate itself about axis 32, this creates a see-saw or oscillating motion about an axis that is generally horizontal and perpendicular to axis 32. That horizontal axis about which sample connector 60 oscillates moves slightly to and fro as sample connector 60 is operated, and its motion is dampened by the springs that help secure sample connector 60 to housing 10.

The application uses small metal balls, ceramic balls or other glass media to "grind" or pulverize the sample. After a ball is inserted into a sample container or titer plate of acceptable size, the samples are moved vertically up and down at a high rate of speed due to the rotation of the horizontally oriented shaft 30, which causes the balls, in their motion, to breakdown the material in the sample container. The vial, which contains a single sample with one or more balls, or multiple sample vials each with their own media selection, is shaken in a complex motion that combines back-and-forth swings with short lateral movements, each end of the vial moving along a figure-8 path. This motion develops strong G-forces in the vial, to pulverize the toughest rocks, slags, and ceramics. The beads or balls within the vials are not bottomed out at either end of the vial for very long before they are thrown in a different direction. The bead beating technique can be used with balls or other media ranging in size from less than 100 microns to as large as 25 mm. The media can be materials such as steel, plastic, Zirconium, Garnet, glass and many others. While any media can be used in a bead beating machine, the ball selection depends upon the vial size, the sample size and hardness to be disrupted, the sample sensitivity to heat, media contamination concerns and many other factors.

Bead beater 100 incorporates several bearings, including two double bearings assemblies. The first bearing assembly 50 is designed to protect bead beater 100 from excessive wear and tear from the moving mechanism, i.e. sample connector 60 attached to shaft 30. As shown in FIG. 1, bearing assembly 50 is located within a housing that is anchored to damper plate 40. The motion of sample connector 60 can inflict a considerable shifting axial load onto the motor shaft 30, which can reduce motor life. Bearing assembly 50 located between sample connector 60 and motor 20 protects motor 20 primarily by preventing shaft 30 from impacting motor 20 along its axis 34. That is, the motion of sample connector 60 directs force along axis 34 of shaft 30 toward motor 20, and the presence of bearing assembly 50 greatly lessens the impact of these forces on motor 20 to protect it and extend the life of bead beater 100. Bearing assembly 50 avoids the need to replace parts in bead beater 100 at such an early stage of the use of the product. A second bearing assembly 61 similar to bearing assembly 50 is disposed within sample connector 60 for interaction with pin 34, and provides similar protection to sample connector 60. Another bearing is disposed within motor 20 itself.

Figure 6:
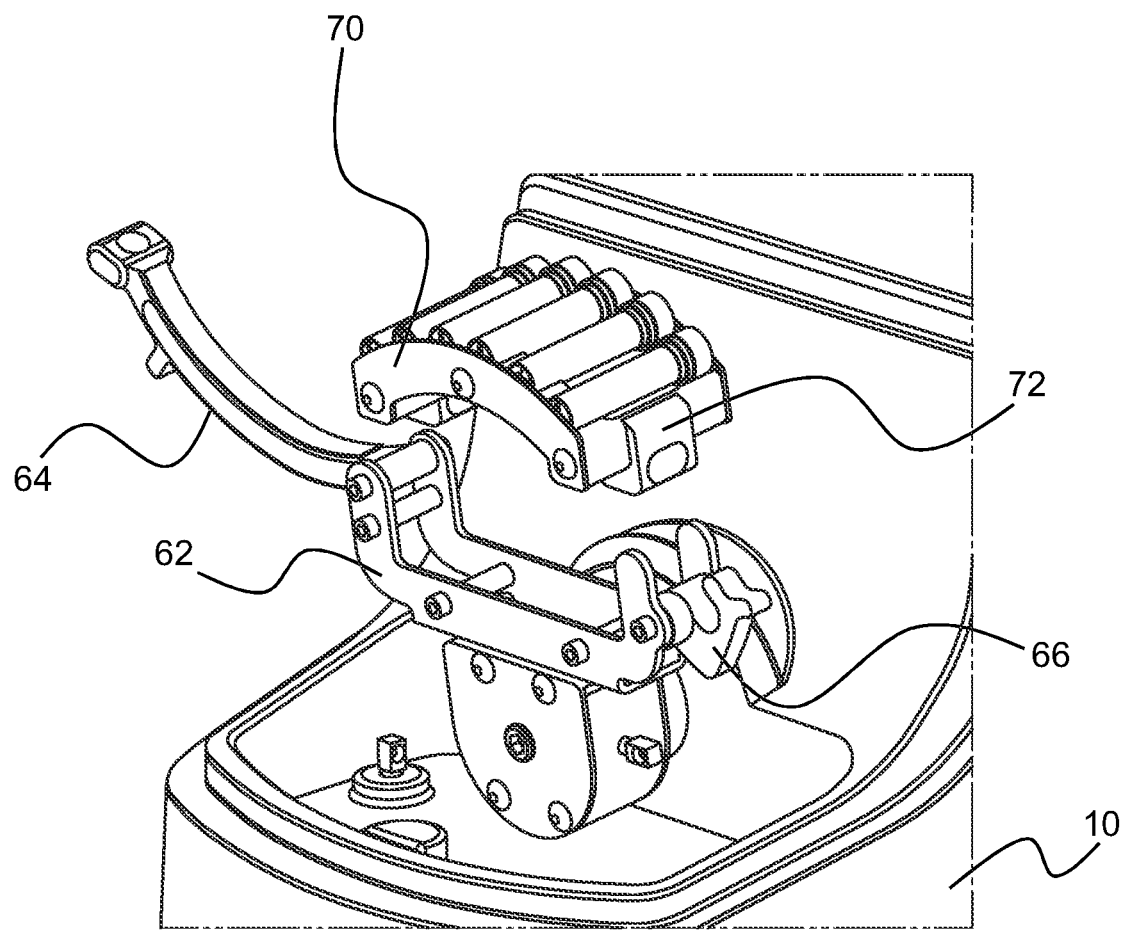
FIG. 6 is an exploded view of a sample vial holder with the bead beater shown in FIG. 1.
Figure 8:
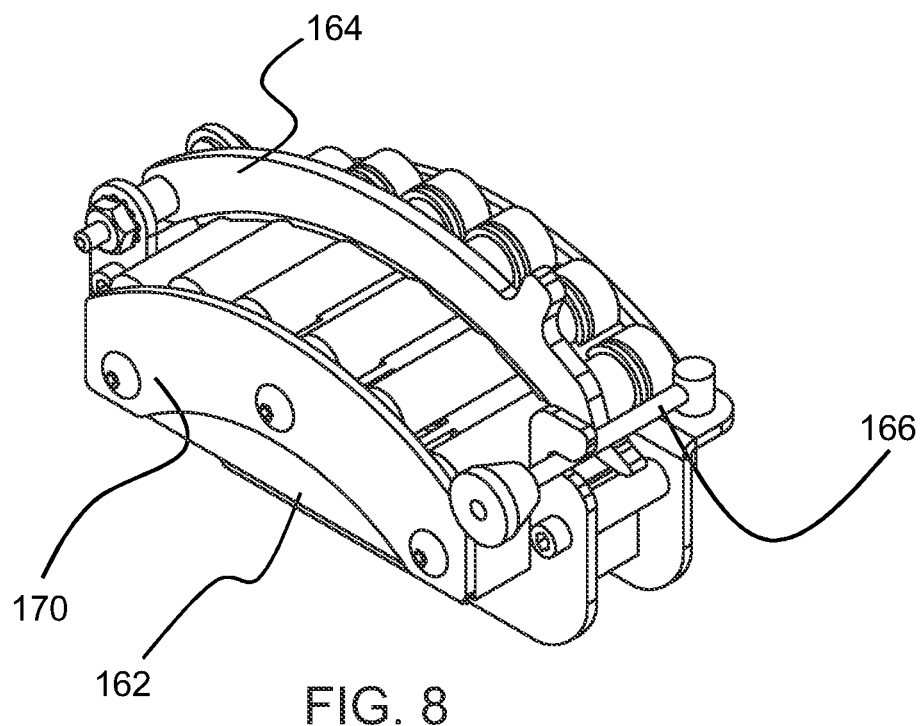
FIG. 8 is a perspective view of another clamping mechanism in accordance with the present invention.
Figure 9A:
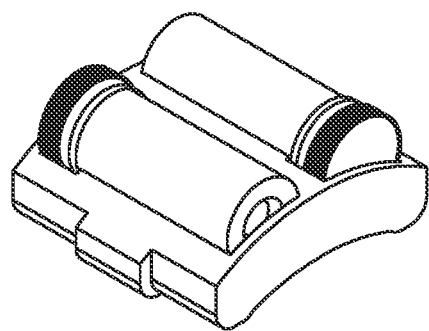
FIGS. 9A-9C show perspective views of three examples of sample cartridges or vial holders.
Figure 9B:
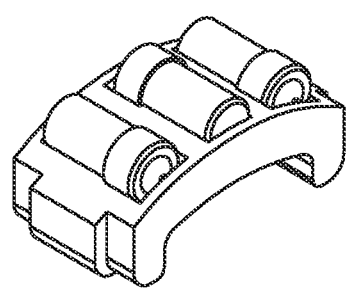
Figure 9C:
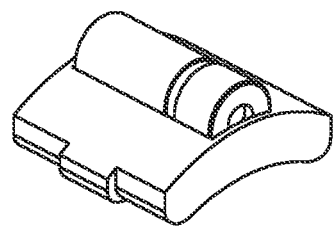
Figure 10A:
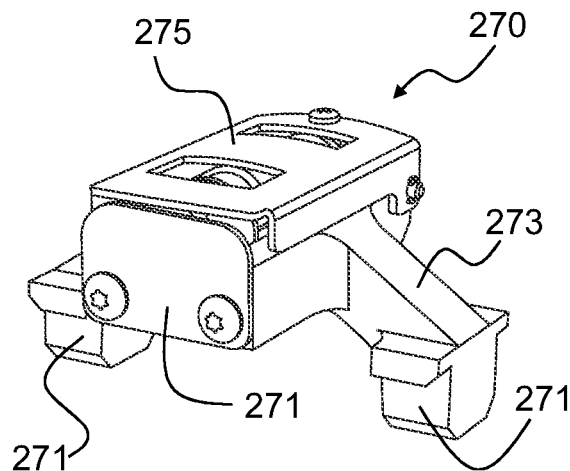
FIGS. 10A-F are perspective assembly, perspective exploded, top, side, front, and rear views, respectively, of another sample vial holder in accordance with the present invention.
Figure 10B:
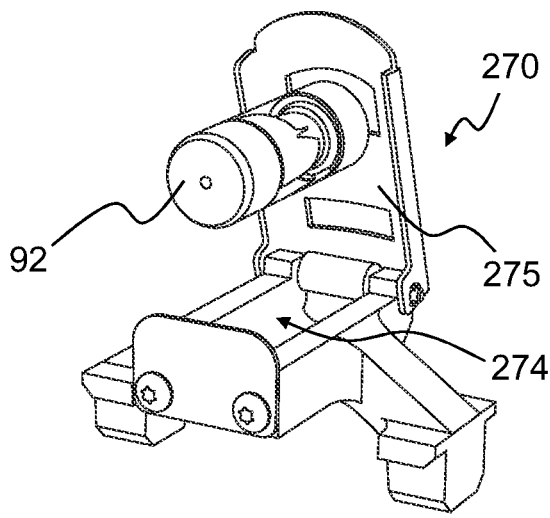
Figure 10C:
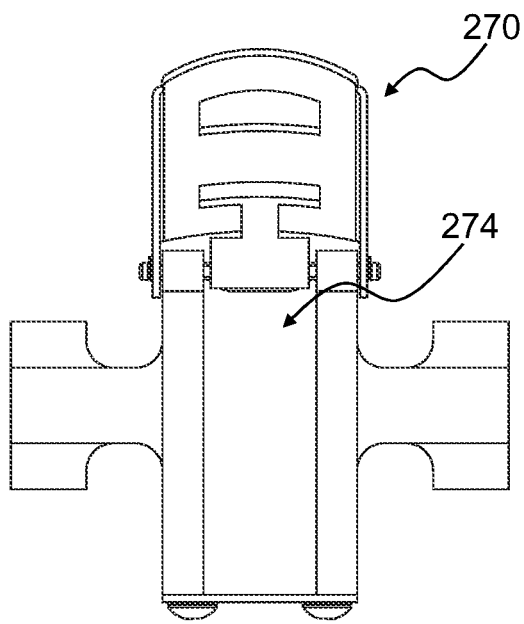
Figure 10D:
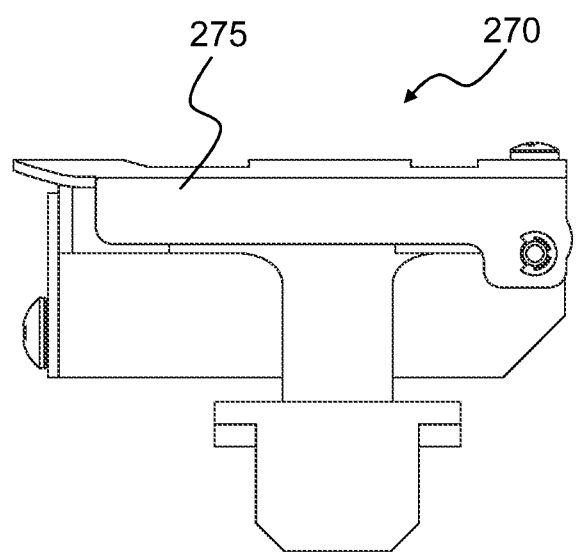
Figure 10E:
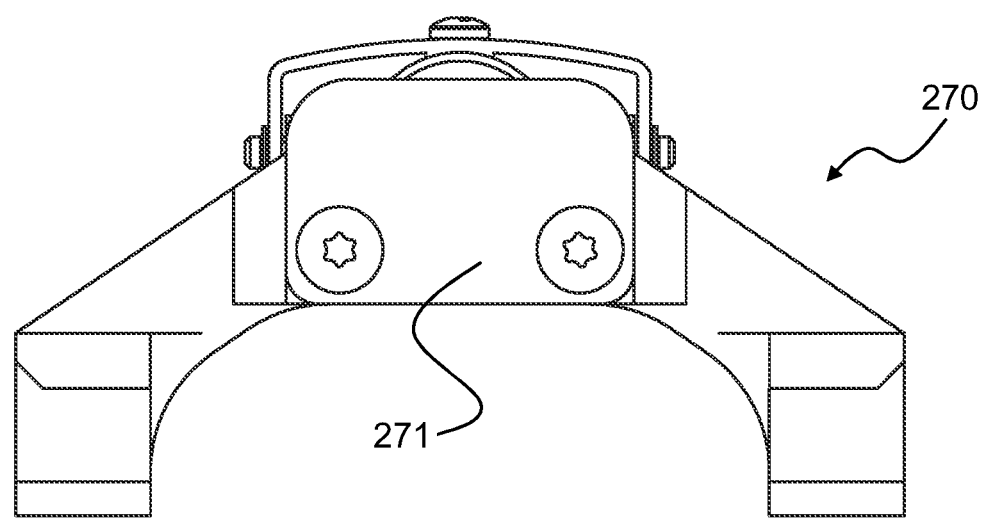
Figure 10F:
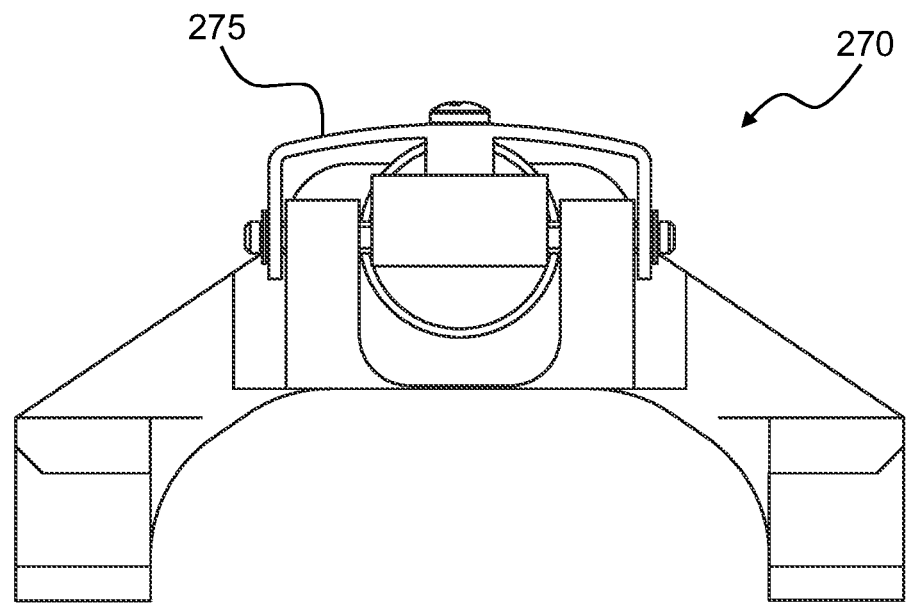

Sample connector 60 is configured to connect with a sample vial holder 70 through a novel clamping arrangement. Sample vial holder 70 is located within a clamp base 62 that is securely mounted on or anchored to the top of sample connector 60 so that clamp base 62 moves with the rest of sample connector 60. A clamp arm 64 is pivotally connected at one side of clamp base 62 via a pin or bolt 67 so that it can swing toward and away from clamp base 62. A clamp latch 66 is pivotally connected to the other side of clamp base 62. The vial holder 70 has wings 72 that are shorter than its overall width and protrude outward from each side, so that they can sit between two arms of clamp base 62. This secures vial holder 70 in the horizontal direction along axis 32, while clamp base 62 and clamp arm 64 further secure vial holder 70 in the other horizontal and vertical directions. When clamp arm 64 is closed over the top of sample vial holder 70 and the vials therein, clamp latch 66 can be pivoted to lock clamp arm 64 securely in place. Altogether, the components of sample connector 60 securely and reliably hold sample vial holder 70 and the vials therein in its operable condition throughout the high levels of agitation and vibration and throughout the duration of the bead beating process. This vial holder mounting mechanism is unique in its form factor and application use which serves to preserve the integrity of the vial containers. FIG. 6 shows the sample holder insertion and the locking arm 64 to secure the holder 70. FIG. 8 shows another clamping mechanism in accordance with the present invention, and in particular, a sample holder 170, cartridge, clamp base 162, retaining arm 164, and locking mechanism assembly 166. Locking mechanism assembly 166 includes a horizontally-oriented bar that swings toward retaining arm 164 and pins a distal end of retaining arm 164 beneath it while being locked within a slot of clamp base 162.

Bead beater 100 is designed to operate with a great variety of materials that come in all different sizes and can be ground with different pulverizing medium. One benefit of the design of bead beater 100 is that it can accommodate and securely hold several different types of interchangeable sample vial holders, which allows for different numbers and sizes of vial types to be used according to need. This design feature allows bead beater 100 to handle widely different vial form factors.

For example, among the sample vial holders for use in bead beater 100 in bead beater (i.e. grinding) or mixing mode, the following are provided in particular. A first sample vial holder holds six (6) 2 ml plastic vials each having a screw-on cap. A second sample vial holder holds four (4) 5 ml plastic vials each having a screw-on cap or a slip-on cap. A third sample vial holder holds two (2) 2 ml cooled sample containers. A fourth sample vial holder holds two (2) 1 ml Hardened Tool steel vial sets. A fifth sample vial holder holds one (1) 1.6 or 3.5 ml Agate vial set. A sixth sample vial holder holds one (1) 5 ml Hardened Tool Steel vial set made, for example, of tungsten carbide. A seventh sample vial holder holds one (1) to four (4) 7 or 12 ml plastic vials. These are just some examples of vial holders that can be used with bead beater 100. As can be appreciated, different vial holders can be designed to hold different quantities and sizes of different types of vials according to need. For example, typical sample vials sizes are in the range of 2 milliliters to 7 milliliters. Some instruments accommodate sample container sizes in excess 75 milliliters. Vial sizes range between 2 ml and 50 ml. Some instruments limit the vial size selection to 2 ml, 5 ml and 7 ml while other units accept these vials and others like 75 ml vials, titer plates, 50 ml QuEChERS vials and many others. They can accommodate a full range of sample vials from 2 mL to 50 mL centrifuge tubes or up to six deep-well titer plates.

Figure 4:
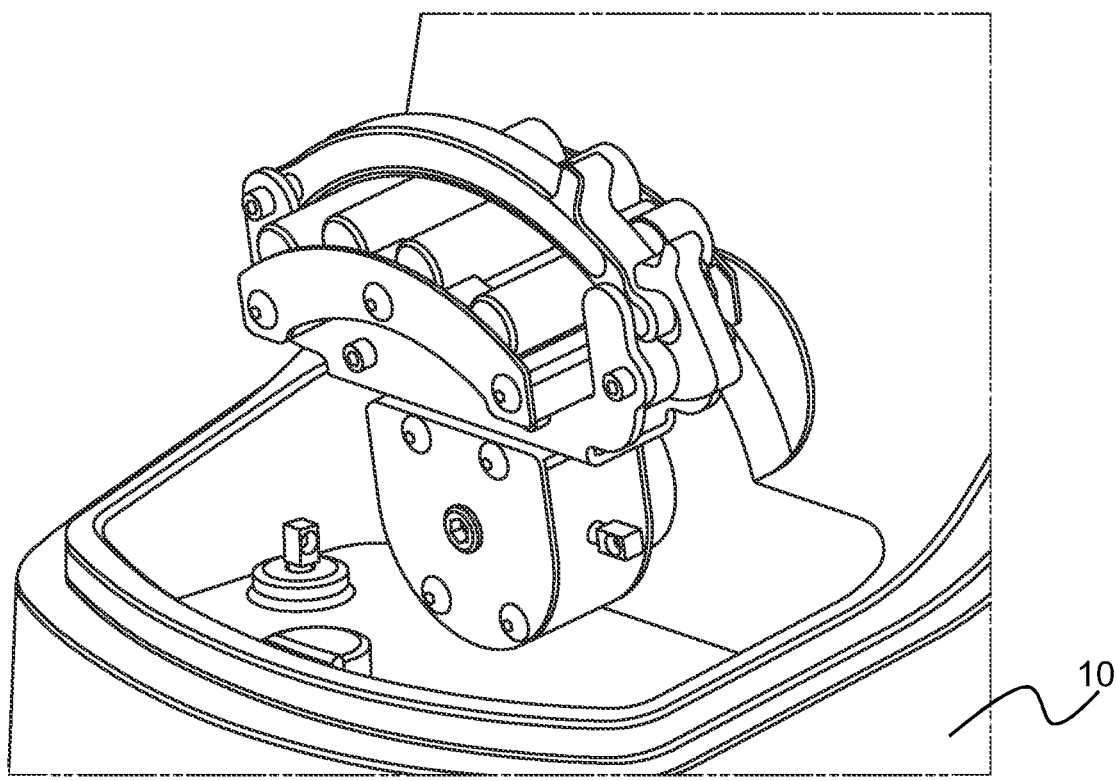
Figure 5:
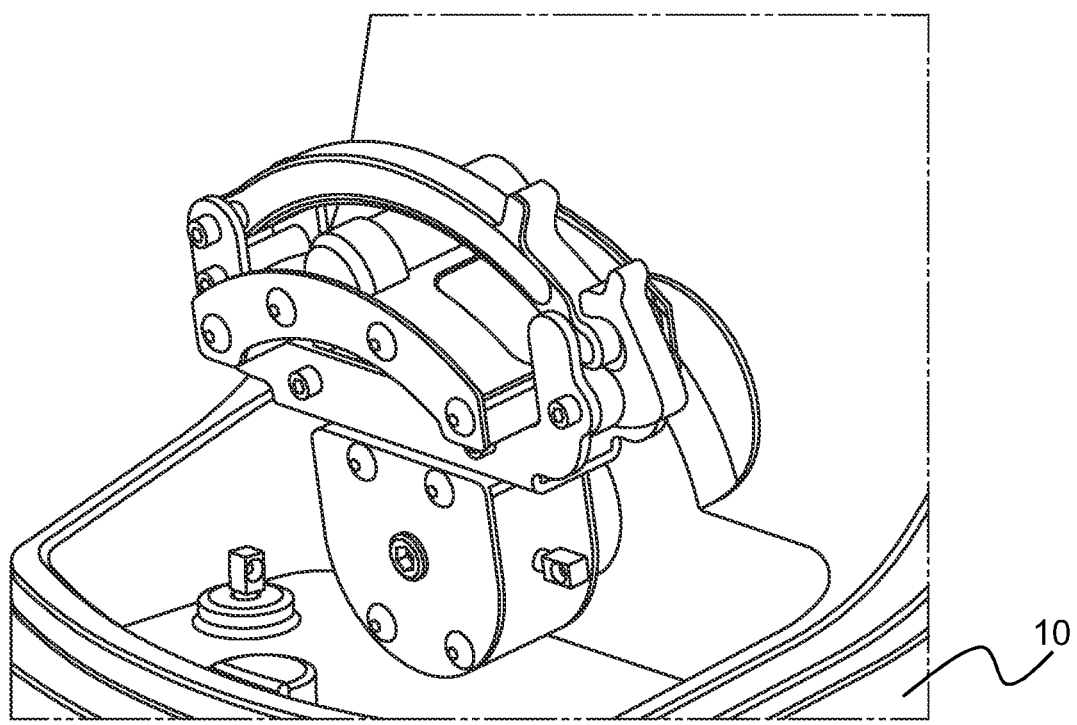

FIGS. 3-5 show three different sample vial sizes with different sample holders for each vial type. More specifically, FIG. 3 shows 2 ml vials, FIG. 4 shows 5 ml vials, and FIG. 5 shows a 5 ml Carbide Steel vial. Each vial holder has the same footprint so that it can be utilized with sample connector 60, and more specifically, the same clamp base 62, clamp arm 64, and clamp latch 66.

Unlike other cell lysing and homogenizing devices, bead beater 100 is not limited to cell lysing and homogenizing alone. It is able to use other types of sample vials to grind rocks, glasses, cement, catalysts and other brittle samples. These sample vials either have metal ends or are reinforced with metal at each end so that they can withstand the stronger forces due to the brittle, hard nature of these types of samples. Bead beater 100 can be used for sample preparation related to elemental analysis and particle size analysis using technologies like XRF spectroscopy and Inductively coupled plasma (ICP) emission spectroscopy. The unit is able to support heavier temperature sustaining vial assemblies to help temperature sensitive samples by limiting the temperature rise associated with the Bead Beating process. No other instrument can handle the number of sample containers for applications ranging from cell lysing to mechanical grinding, allowing the grinding of rocks into a powder.

In addition to using stronger vials, the sample vial holders 70 in connection with bead beater 100 have stronger and larger end walls 71, as shown in FIG. 3. The wells for each vial are deeper so that end walls 71 cover more of the area of each of the top and bottom ends of each vial. In one embodiment, end walls 71 can each cover more than 50% of the area of each end face of the vial, respectively. In other embodiments, end walls 71 can each cover 60%, 70%, 80%, 90%, or another percentage of the area of each end face of the vial. In other embodiments, one or both end walls 71 can be contoured to completely cover the end of vials. This reinforces the strength of the ends of each vial so that the balls or other medium used for grinding do not wear down the vials as quickly during agitation and operation of bead beater 100.

FIGS. 10A-F show another vial holder 270 for one (1) metal 5 mL vial 92, which can be steel capped or tungsten carbide capped. Vial holder 270 is designed to hold vials 92 that grind/pulverize very hard materials like small rocks. A base 273 of vial holder 270 supports the chamber area 274 in which vial 92 is disposed. A lid 275 pivots via a bolt or screw at one end of chamber 274 so that it can cover chamber 274 once vial 92 is placed inside. The other end of chamber is provided with end wall 271 to further secure vial 92. Wings 272 of base 273 extend downward and mate with sample connector 60, which covers and clamps vial holder 270 as described above to secure vial 92 in place during use. Lid 274 need not be secured to end wall 271 separately, since vial holder 270 will only be operated within sample connector 60. That is, clamp arm 64 secures lid 275 in place during use so that chamber 274 is secure. Vial holder 270 provides another embodiment of a secure holder for a vial of a different type so that bead beater 100 can accommodate these harder and more brittle samples.

Figure 11A:
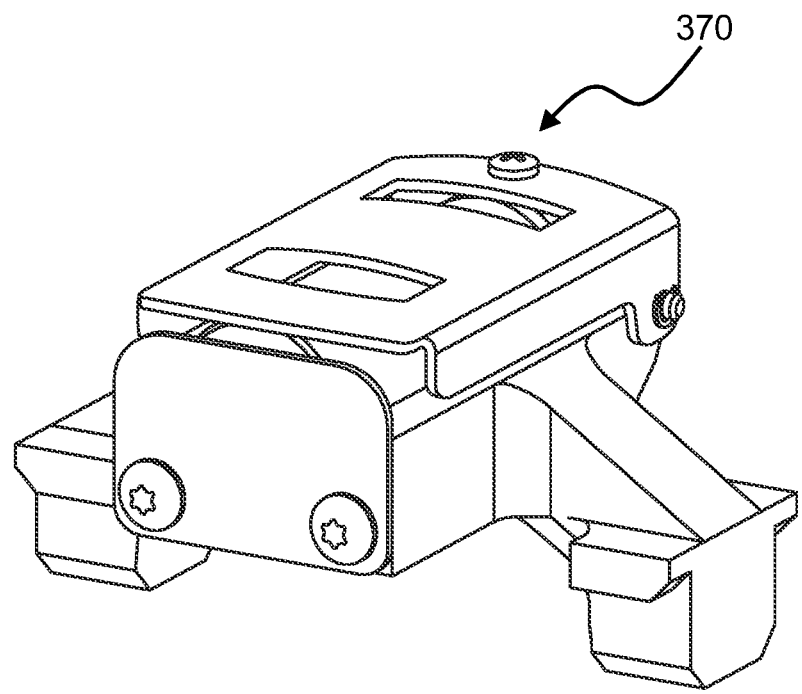
FIGS. 11A-B are perspective assembly and perspective exploded views, respectively, of another sample vial holder in accordance with the present invention.
Figure 11B:
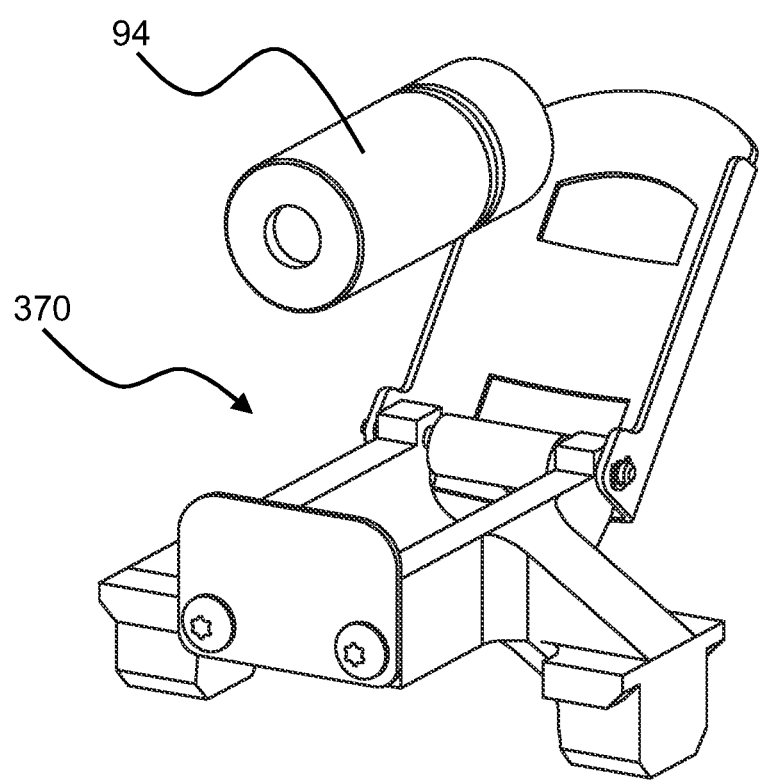

FIGS. 11A and 11B show another variation of a vial holder 370 that is similar to vial holder 270. Vial holder 370 is designed for one (1) 3.5 mL agate vial 94 used to grind hard materials that require an iron free sample holder. Both vial holders 270 and 370 compress the vial lid onto the vial when clamp arm 64 is in place to prevent sample powder from escaping the vial.

Figure 12:
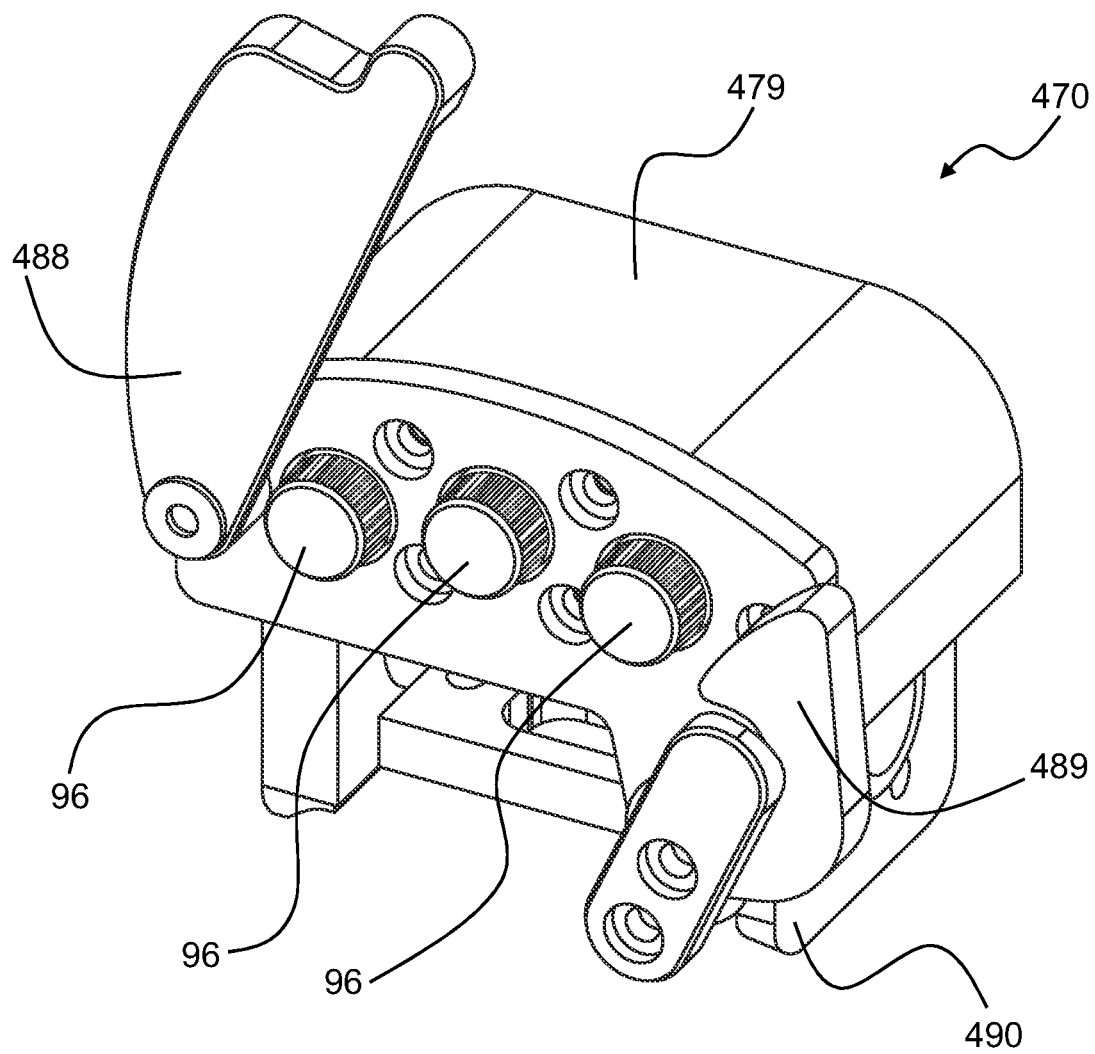
FIG. 12 is a perspective view of a sample vial holder in accordance with the present invention.
Figure 13A:
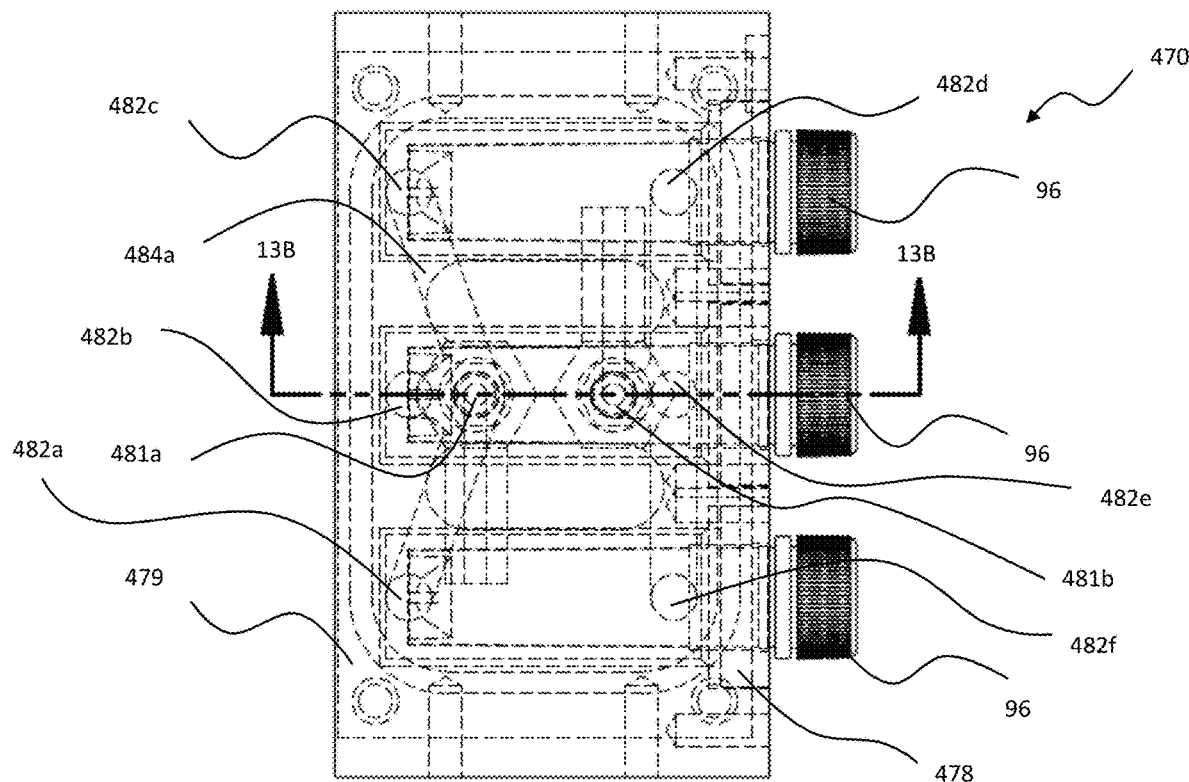
FIGS. 13A-B are bottom and cross sectional side views, respectively, of the sample vial holder shown in FIG. 12.
Figure 13B:
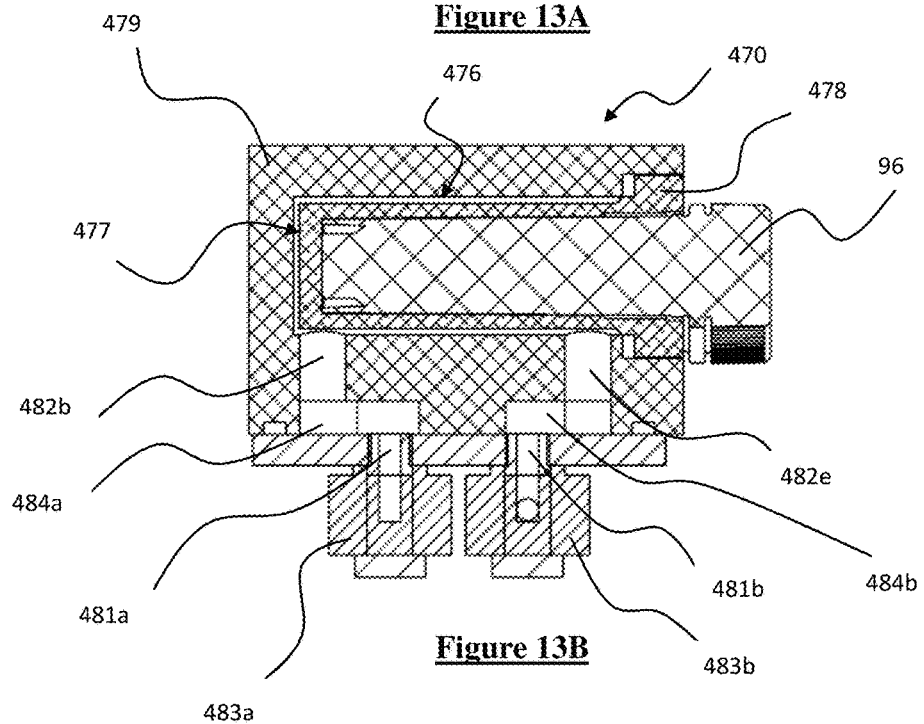

As shown in FIGS. 12, 13A, and 13B, one type of sample vial holder 470 according to the present invention is a holder for a cooled sample vial 96. All high energy bead beating machines warm the sample within at a rate of about 10 degrees Celsius per minute. This is due to frictional collisions of the beads during homogenization. An improved cooled vial assembly is provided to counteract the warming tendency of the machine operation. The cooled vial assembly uses a refrigerated circulator providing temperature stability to the sample holder 470 including a dry air purge to reduce condensation.

A series of channels is provided in sample connector 60, sample vial holder 70, and/or the vials themselves in order to pass cooled liquid throughout the agitation process of bead beater 100. These channels can be connected through shaft 30 so that they can be accessed from the inside of housing 10 during operation of the device. This allows the temperature of the sample to be maintained at a certain level throughout the process. Prior art devices that use pre-cooled blocks do not have the same ability to continuously affect and control temperature during operation of the machine.

Vial holder 470 includes a housing 479 having cavities 477 in which vials 96 are disposed. Each cavity 477 first seats a holder plug 478 that itself has a cavity for vial 96 to be inserted. Holder plug 478 is seated in cavity 477 such that the flange at its open end seals cavity 478 to the external environment, and in some cases can do so with an o-ring or gasket. This creates a thin pocket 476, shown in FIG. 13B, that encompasses holder plug 478 so that cooling material can flow throughout pocket 476 and around holder plug 478.

A network of flow channels 482a-f are accessed by flow ports 481a-b at a lower end of housing 479. Flow ports 481 are connected to inlet and outlet hoses that are secured by nuts 483a-b in order to provide and allow the exit of cooling fluid from vial holder 470. These hoses can extend through bead beater 100 and can be connected to a pump and a coolant reservoir, so that bead beater 100 can circulate the cooling fluid. Flow port 481a leads to a disbursement channel 484a, which in turn leads to flow channels 482a-c. These flow channels 482a-c lead to respective pockets 476 so the cooling fluid can be channeled from the inlet hose into engagement with each holder plug 478. Flow channels 482d-f then allow the cooling fluid to exit pockets 476 into a collection channel 484b, which empties the cooling fluid into flow port 481b and out the outlet hose. Cooling fluid, such as water, a mixture of water and ethylene glycol, or any other type of fluid that can maintain very low temperatures, for example at or below the freezing point of water, and achieve proper circulation though the system, can be provided at a constant temperature and circulated through this path so that it can absorb heat from the vials through the holder plugs 478 to continuously maintain a lower desired operating temperature during grinding of the samples within the vials.

Vial holder 470 has a cover guard 488 that clips into a latch 489 so that the cap ends of the vials can be securely retained within the receptacles during use. Cover guard 488 is thinner at its lower end to present a relief at the side facing the vials so their caps can be accommodated and shielded. A lower attachment 490 is provided for connection to sample connector 60. In particular, the bottom frame portion of vial holder 470 has a central relief area to allow a connection with the external hoses for fluid circulation, and also has side frames with windows that allow sample connector 60 to clamp vial holder 470 in a manner similar to the above, although with clamp arm 64 extending through the frame instead of around the entire vial holder.

In another embodiment, a sample vial or sample vial holder 70 can include a phase change material (PCM) in its walls that has the ability to maintain low temperatures better than cooled metal as presently used in prior art devices. A phase change material (PCM) product from PureTemp, such as PureTemp 4 PCM material, has been used in experiments that has properties such that a large amount of thermal energy is required to allow a phase change from a solid to a liquid or liquid to a solid. The PureTemp 4 material has a melting point of 4 degrees Centigrade. A PCM, like PureTemp 4, can stay colder longer, after it has reached a solid frozen state, because of the higher thermal energy this material must absorb before "melting". The PCM can absorb significant heat from the sample holder and sample that might otherwise increase the temperature to an unacceptable level for some samples like RNA. During the RNA sample grinding process for DNA extraction, it is necessary to keep the sample below 4-5 degrees Centigrade. During a sample grinding experiment, the sample temperature will increase due to the violent interaction of steel balls inside the vials.

An experiment was run using 2.5 grams of PCM inserted into a cavity of a 2 vial sample holder and secured within the cavity to prevent leakage. The PCM cavity was located between two 2 ml sample vials. The holder with vials was placed into a normal refrigerator freezer for 1.5 hours and tested for the temperature rise in a 1 minute "grinding" experiment at 4,000 rpms in the GenoLyte by SPEX SamplePrep, LLC wherein the 2-millimeter vials contained 1 milliliter of water and seven 2.8 mm steel balls. As noted below, the use of PCMs is reducing the sample heating has proven to be very successful. Under normal grinding conditions the outside surface of the vial, the increased 15 degrees Centigrade while the outside vial surface only increased 3.5 Degrees with the PCM integrated into the sample vial holder. The use of such materials for use in sample grinding methods can be extended to many instruments, including the GenoGrinder, MixerMill and MiniG products by SPEX SamplePrep, LLC.

Figure 7:
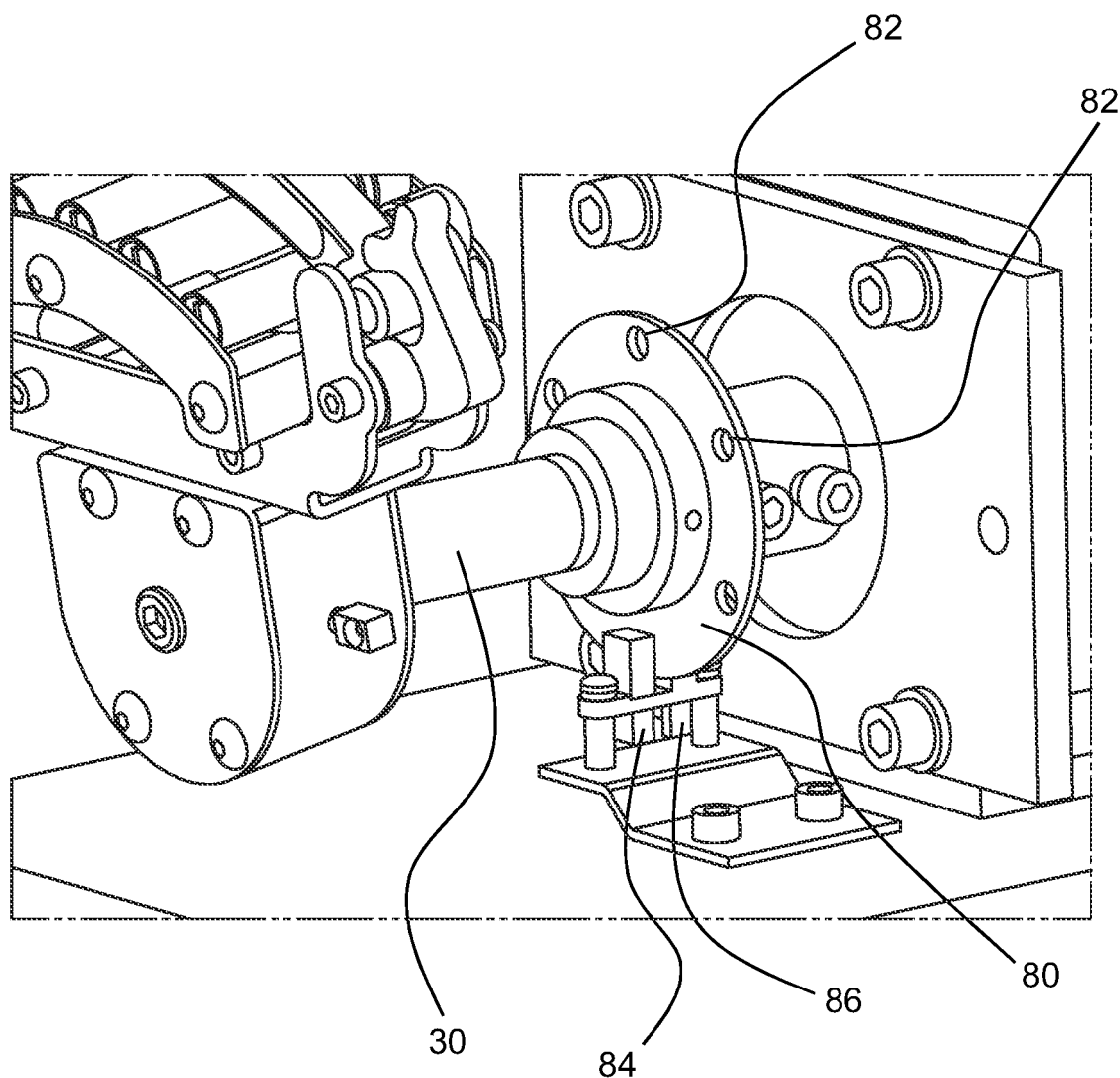
FIG. 7 is a perspective view of a speed control mechanism in the bead beater shown in FIG. 1.

Bead beater 100 includes a speed control mechanism that operates independent of the weight of the vial and sample mass as the speed is measured for each single use and maintained during the grinding to ensure that the set speed is maintained. This ability is afforded by a measurement disc 80 rotationally coupled with the shaft 30 for rotation therewith. Disc 80 includes several apertures 82 and is positioned so that its peripheral edge and the apertures 82 spin between two plates 84, 86 of an optical interrupter that pass an IR signal therebetween and that are anchored to damper plate 40. The size and/or location of apertures 82 is known and the frequency at which apertures 82 pass between plates 84, 86 and, more specifically, through the path of the IR signal allows a recording of the detected interruptions of the IR signal. This interruption corresponds to the passing of the solid portions of disc 80 between apertures 82. This allows bead beater 100 to determine the rotational speed of shaft 30 as follows. Plates 84, 86 are in communication with a processor that receives signals corresponding to the interruption of the IR signal. The processor then calculates the frequency of these interruptions given the known radial distance of each aperture 82 from the central axis 32 of shaft 30 and also given the known arc length between successive apertures 82, which is a constant value for all adjacent pairs of apertures 82 in disc 80. The duration of one complete rotation of shaft 30 can then be determined, from which angular or rotational velocity can be determined. FIG. 7 depicts these components, demonstrating how the speed is actively measured in real time to confirm the actual speed setting.

Bead beater 100 includes a digital display that can allow the user to provide input, such as time, speed, etc., and can provide a readout for the user of the same metrics.

Bead beater 100 and the various new components of same described herein are useful in several markets and applications, including the following.

Agriculture: used for Plant Research and Crop Science, Residual Pesticide analysis, Food safety, Disease research, Protein extraction, Soil studies, Bio-Fuels, etc. Target customers would include crop research companies, environmental and agriculture testing companies and agencies, pesticide and fertilizer manufacturers, etc.

Forensics: used for human identification, drug abuse, toxicology, etc. Target customers would include police laboratories, contract testing labs, archaeology labs, government labs, etc.

Mining & cement: used for grinding and pulverizing of cement and ore. Target customers would include mining production companies, steel mills, contract testing labs, cement production, government agencies, etc.

Pharmaceutical/medical research: used for DNA extraction, mixing and blending, quality control, disease research, contamination testing, protein extraction, etc. Target customers would include pharmaceutical research companies, disease research institutes, biotechnology companies, contract testing labs, etc.

Materials research: used for mechanical alloying, mixing and blending, cryogenic grinding, sample size reduction for elemental research (for example RoHS) and sample size reduction for pressing pellets and sample measurement. Target customers would include university engineering and materials science departments, battery manufacturers, solar power companies, automobile companies, aeronautical companies, polymer production companies, contract testing labs, recycling companies, packaging companies, electronic goods manufacturers, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A bead beater homogenizer comprising:
 a shaft having a main body extending along a main axis and a distal connection body extending along a connection axis that is acutely angled with respect to the main axis;
 a housing containing a motor configured to rotate the shaft about the main axis;
 a head rotatably connected to the distal connection body of the shaft and connected to the housing by a first spring on a first side of the shaft and a second spring on a second side of the shaft;
 a clamp secured to the head and configured to secure a sample vial holder configured to hold one or more sample vials therein;

a speed measurement disc rotationally coupled with the main body of the shaft, wherein the speed measurement disc defines a plurality of apertures in a circumferential periphery thereof; and an optical interrupter having two plates between which an IR signal is passed, wherein rotational motion of the shaft about the main axis is translated into motion of the head in directions normal to the main axis, wherein the main body of the shaft intersects with the distal connection body at a bend or elbow in the shaft, wherein the distal connection body is disposed within a lumen defined by the head, and wherein the circumferential periphery of the speed measurement disc is disposed between the plates of the optical interrupter such that the apertures cross a path of the IR signal.

2. The bead beater homogenizer of claim 1, wherein rotational motion of the shaft about the main axis is also translated into oscillating motion of the head such that an end of the head closest to the main body of the shaft is pivoted toward and away from the main body of the shaft.

3. The bead beater homogenizer of claim 1, wherein the clamp includes a clamp base in which the sample vial holder can be disposed, a clamp arm connected to the clamp base, and a clamp latch connected to the clamp base, wherein engagement of the clamp latch with the clamp arm secures the sample vial holder to the head.

4. The bead beater homogenizer of claim 1, further comprising a plurality of differently configured sample vial holders.

5. The bead beater homogenizer of claim 4, wherein the differently configured sample vial holders include at least two of:
a first sample vial holder having only one well to hold one vial;
a second sample vial holder having only two wells to hold two vials;
a third sample vial holder having only three wells to hold three vials;
a fourth sample vial holder having only four wells to hold four vials;
a fifth sample vial holder having only five wells to hold five vials;
a sixth sample vial holder having only six wells to hold six vials; and
a seventh sample vial holder having at least one well to hold a vial and an internal network of channels through which a coolant can be passed to control a temperature of a vial disposed therein.

6. The bead beater homogenizer of claim 1, further comprising a sample vial holder defining an internal network of channels through which a coolant can be passed to control a temperature of a vial disposed therein.

7. The bead beater homogenizer of claim 6, wherein the sample vial holder includes a housing defining a cavity configured to at least partially enclose a vial, and wherein the internal network of channels includes an inlet channel, an internal channel adjacent the cavity, and an outlet channel connected for flow of the coolant.

8. The bead beater homogenizer of claim 6, wherein the sample vial holder includes a housing defining a cavity configured to at least partially enclose a vial, and a holder plug disposed in the cavity to seal the cavity from an external environment, the holder plug defining a cavity in which a vial can be seated.

9. The bead beater homogenizer of claim 8, wherein an empty pocket is defined between an internal surface of the cavity of the housing and an external surface of the holder plug.

10. The bead beater homogenizer of claim 9, wherein the internal network of channels includes an inlet channel leading to the empty pocket, and an outlet channel leading away from the empty pocket, such that the inlet channel, the empty pocket, and the outlet channel define a passage through which a coolant can be passed to control a temperature of a vial disposed in the holder plug.

11. The bead beater homogenizer of claim 1, further comprising a first bearing assembly disposed about the shaft between the head and the motor, wherein the head further comprises a second bearing assembly disposed about the distal connection body of the shaft, and wherein the motor includes a third bearing assembly.

12. The bead beater homogenizer of claim 1, further comprising a processor that receives signals corresponding to the interruption of the IR signal and that is configured to use the signals to calculate rotational speed of the shaft.

13. The bead beater homogenizer of claim 1, wherein rotational motion of the shaft about the main axis rotates the distal connection body such that the distal connection body sweeps out an imaginary conical surface.

14. The bead beater homogenizer of claim 13, wherein rotational motion of the shaft about the main axis rotates the head in a circular path on an imaginary conical surface.

15. A bead beater homogenizer comprising:
a shaft having a main body extending along a main axis and a distal connection body extending along a connection axis that is acutely angled with respect to the main axis;
a house containing a motor configured to rotate the shaft about the shaft axis and including a first bearing assembly;
a head rotatably connected to the distal connection body of the shaft and connected to the housing by a first spring on a first side of the shaft and a second spring on a second side of the shaft, wherein the head comprises a second bearing assembly disposed about the distal connection body of the shaft;
a sample vial holder secured to the head;
a third bearing assembly disposed about the shaft between the head and the motor;
a speed measurement disc rotationally coupled with the main body of the shaft, wherein the speed measurement disc defines a plurality of apertures in a circumferential periphery thereof; and
an optical interrupter having two plates between which an IR signal is passed,
wherein the main body of the shaft intersects with the distal connection body at a bend or elbow in the shaft,
wherein the distal connection body is disposed within a lumen defined by the head, and
wherein the circumferential periphery of the speed measurement disc is disposed between the plates of the optical interrupter such that the apertures cross a path of the IR signal.

* * * * *